United States Patent [19]

Koizumi et al.

[11] 4,290,953
[45] Sep. 22, 1981

[54] BENZOXAZEPINE DERIVATIVES AND PROCESS FOR PREPARING THE SAME

[75] Inventors: Masuo Koizumi, Mizumotoiizuka; Kazuo Sasahara, Ohmiya; Yasushi Murakami, Tokyo; Sakae Wada, Kashiwa; Hiroshi Nakakimura, Kamakura; Noboru Kubodera, Saitama; Shun-Ichi Hata, Yokohama, all of Japan

[73] Assignee: Chugai Seiyaku Kabushiki Kaisha, Tokyo, Japan

[21] Appl. No.: 100,437

[22] Filed: Dec. 5, 1979

[30] Foreign Application Priority Data

Dec. 6, 1978 [JP] Japan .................................. 53-149934

[51] Int. Cl.³ .......................................... C07D 498/00
[52] U.S. Cl. ...................................... 260/333; 424/244
[58] Field of Search ........................................... 260/333

[56] References Cited

U.S. PATENT DOCUMENTS

| | | | |
|---|---|---|---|
| 3,458,516 | 7/1969 | Howell et al. | 260/333 |
| 3,793,345 | 2/1974 | Yale et al. | 260/333 |
| 4,045,442 | 8/1977 | Mueller | 424/244 |
| 4,125,532 | 11/1978 | Mueller | 544/111 X |
| 4,170,593 | 10/1979 | Mueller | 260/243.3 |

FOREIGN PATENT DOCUMENTS

| | | | |
|---|---|---|---|
| 850104 | 5/1977 | Belgium | 260/333 |
| 2547651 | 4/1977 | Fed. Rep. of Germany | 260/333 |
| 1522003 | 8/1978 | United Kingdom | 260/333 |

*Primary Examiner*—Ethel G. Love
*Attorney, Agent, or Firm*—Browdy and Neimark

[57] ABSTRACT

Dibenz[b,f][1,4]oxazepine derivatives represented by the formula

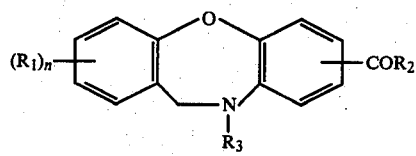

[wherein $R_1$, n, $R_2$ and $R_3$ are as defined in the specification], and a process for preparing the same are disclosed. The object compounds have excellent serum cholesterol lowering activity, serum lipid lowering activity, blood lipid peroxide lowering activity and anti-aggregation of platelet activity, and therefore are useful as a drug.

24 Claims, No Drawings

BENZOXAZEPINE DERIVATIVES AND PROCESS FOR PREPARING THE SAME

This invention relates to a dibenz[b,f][1,4]oxazepine derivative represented by the formula

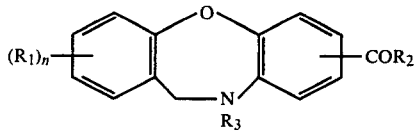

[wherein $R_1$ is hydrogen, a halogen, a lower alkyl group or a lower alkoxyl group; n is an integer of 1 or 2; $R_2$ is a hydroxyl group, a lower alkoxyl group or a nuclear-substituted or unsubstituted anilino group; and $R_3$ is hydrogen or an acyl group], and a process for preparing the same.

The compound of the formula (I) has serum cholesterol lowering activity, serum lipid lowering activity, blood lipid peroxide lowering activity and anticoagulant activity, and therefore is useful as a drug.

The object compound of this invention is prepared by reducing and cyclizing a diphenyl ether derivative represented by the formula

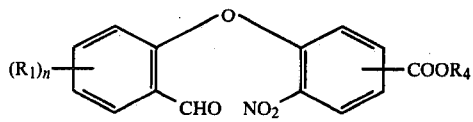

[wherein $R_1$ and n are as defined above and $R_4$ is a lower alkyl group] to form a compound represented by the formula

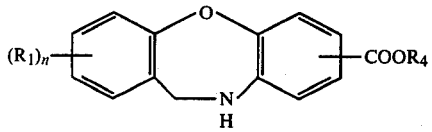

[wherein $R_1$, n and $R_4$ are as defined above]. This compound corresponds to the compound of the formula (I) wherein $R_2$ is a lower alkoxy group and $R_3$ is hydrogen.

The compound of the formula (II) used in the above reaction is novel and can be easily prepared by the reaction of the following equation

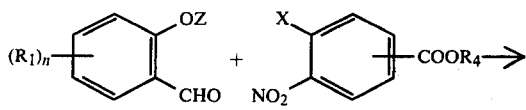

[wherein $R_1$, n, and $R_4$ are as defined above, Z is an alkali metal and X is halogen].

The reduction and cyclization reactions for converting the compound (II) to the compound (III) are carried out by stirring the compounds in a solvent such as methanol, ethanol, dioxane, tetrahydrofuran or the like or a mixture thereof in the presence of 5–10% of Raney nickel, or paradium-charcoal in a hydrogen atmosphere at 30°–80° C., preferably at 40°–60° C. The cyclization is advanced as the reduction of a nitro group of the starting compound progresses.

The compound of the formula (III) is hydrolyzed by a conventional method to form a compound of the formula

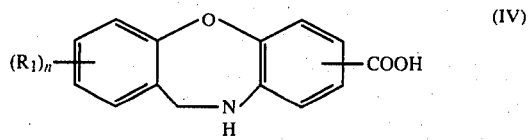

[wherein $R_1$ and n are as defined above], which is equivalent to the compound of the formula (I) wherein $R_2$ is hydroxyl and $R_3$ is hydrogen. This hydrolysis can be conducted, for example, by refluxing the compound of the formula (III) in water, an alcohol or aqueous alcohol in the presence of an alkali such as sodium hydroxide, potassium hydroxide or the like for 30 minutes to 5 hours.

The resulting compound of the formula (IV) can be esterified again by a conventional method to form any type of ester of the formula (III).

Further, the compound of the formula (IV) or its reactive derivative at carboxyl group is reacted with aniline or a nuclear-substituted aniline to form a compound of the formula

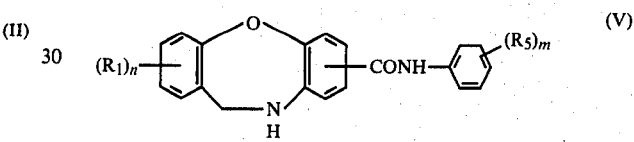

[wherein $R_1$ and n are as defined above; $R_5$ is hydrogen, a lower alkyl group, a lower alkoxyl group or trifluoromethyl group; and m is an integer of 1 or 2].

This reaction can be conducted under conditions used for the conventional amide-formation reaction. For example, it can be carried out in a solvent, such as water, benzene, toluene, tetrahydrofurna, diethyl ether, dioxane, dimethylformamide, chloroform, methylene chloride, pyridine, acetonitrile or a mixture thereof at −10° to 100° C., preferably at 0° to 70° C. The reaction is desirably conducted in the presence of a condensation accelerator such as an inorganic base, for example, a hydroxide, carbonate or acetate of alkali metal or alkaline earth metal; or an organic base, for example, pyridine, triethylamine or picoline. The reactive derivative of the compound of the formula (IV) at carboxyl group includes an acid halide, ester, acid anhydride or mixed acid anhydride with carbonic acid, sulfuric acid, phosphoric acid, sulfonic acid or the like.

The thus formed compound of the formula (III), (IV) or (V) can be converted by subjecting it to a conventional acylation reaction to the corresponding N-acylated compound which is equivalent to the compound of the formula (I) wherein $R_3$ is an acyl group.

A carboxylic acid for acylation of the compound above is used in the form of free acid, anhydride or acid halide and includes fatty acids such as acetic acid, propionic acid, butylic acid, iso-butylic acid, hexonic acid, myristic acid, dichloroacetic acid, dichloropropionic acid and the like; aromatic carboxylic acid such as benzoic acid, benzoic acids nuclear-substituted with at least one halogen, lower alkyl, lower alkoxyl or nitro, phenylacetic acid, cinnamic acid and the like.

This invention is further illustrated by the following Experiments and Examples but they shall not be interpreted as limitative of this invention.

Experiment 1

Male mice (ddY strain) weighing 25-35 g were divided into groups of 10 members each, and intravenously administered with Triton WR-1339 (Ruger Chemicals Co., Inc. N.J. U.S.A.) in a dose of 500 mg/kg. A different test compound listed below was suspended in a 1% aqueous methylcellulose, and the suspension was orally administered twice to each mouse in a dose of 150 mg/kg just after and 6 hours after the administration of Triton. For the control group, only a 1% aqueous methylcellulose was administered. Twenty four hours after the administration of the Triton, the breast of each mouse was incised under anesthesia with diethyl ether and a sample of blood was taken from its heart.

The lipid peroxide level in blood and the cholesterol and triglyceride levels in serum of each sample were measured with RaBA-SUPER (Chugai Seiyaku K.K., Japan) and the percent reduction of each of the levels on the basis of the level of the control was calculated.

The average percent reductions are shown in Table 1 below.

TABLE 1

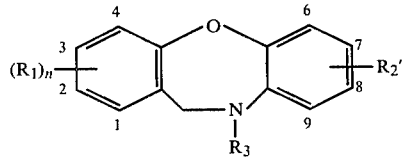

| Substituents | | | Percent Reduction (%) | | |
|---|---|---|---|---|---|
| | | | TC* | TG** | TP*** |
| $(R_1)_n$ | $R_2'$ | $R_3$ | $\bar{x} \pm$ S.E. | $\bar{x} \pm$ S.E. | $\bar{x} \pm$ S.E. |
| H | 8-$CO_2C_2H_5$ | H | 5.2 ± 2.9 | 22.8 ± 3.3 | 19.2 ± 4.2 |
| 2-Br | 8-$CO_2C_2H_5$ | H | 7.9 ± 5.3 | 15.5 ± 3.2 | 11.9 ± 3.3 |
| 4-$OCH_3$ | 8-$CO_2C_2H_5$ | H | 26.4 ± 2.6 | 18.5 ± 4.9 | 21.3 ± 4.5 |
| 4-$OCH_3$ | 8-$CO_2C_2H_5$ | $CH_3$\\$CHCH_2CO-$ / $CH_3$ | 12.9 ± 4.8 | 20.5 ± 2.5 | 10.0 ± 3.1 |
| 4-$OCH_3$ | 8-$CO_2C_2H_5$ | $CHCl_2CO-$ | 16.3 ± 2.9 | 15.6 ± 4.6 | 21.0 ± 6.8 |
| 4-$OCH_3$ | 8-$CO_2C_2H_5$ | Ph-CO- | 11.2 ± 4.7 | 9.9 ± 3.8 | 19.8 ± 5.8 |
| 4-$OCH_3$ | 8-$CO_2C_2H_5$ | $NO_2$-Ph-CO- | 12.0 ± 3.3 | 22.3 ± 4.0 | 19.1 ± 3.8 |
| 4-$OC_2H_5$ | 8-$CO_2C_2H_5$ | 3-$CH_3$-Ph-CO- | 13.6 ± 2.8 | 10.1 ± 6.7 | 13.6 ± 7.0 |
| 4-$OC_2H_5$ | 8-$CO_2C_2H_5$ | $C_2H_5CO-$ | 18.5 ± 4.9 | 28.5 ± 9.8 | 22.1 ± 8.9 |
| H | 6-$CO_2C_2H_5$ | H | 11.4 ± 3.1 | 10.3 ± 6.5 | 15.9 ± 4.0 |

*TC = Cholesterol
**TG = Triglyceride
***TP = Lipid peroxide

Experiment 2

Platelet rich plasma samples were prepared from blood of SD strain rats by the conventional method. A different test compound as a solution in dimethyl sulfoxide (DMSO) was added to each of the assay media in an amount such that the concentration of the test compound in the mixture became $2.5 \times 10^{-4}$ M. For the control, DMSO alone was added to the assay medium. After incubation for one minute, arachidonic acid was added to the assay medium at a concentration of $10^{-4}$ M thereby aggregating the platelet. The aggregation level was determined by an aggregometer, CORNING-EEL MODEL 169 (manufactured by Evans Electro Selenium Ltd.) and the percent inhibition of platelet aggregation was calculated by the following equation.

$$\text{Percent inhibition} = 1 - \frac{\text{aggregation level by test compound}}{\text{aggregation level by DMSO alone}} \times 100$$

The results are shown in Table 2 below.

TABLE 2

| Substituents | | | Percent Inhibition of Platelet Aggregation % |
|---|---|---|---|
| $(R_1)_n$ | $R_2'$ | $R_3$ | |
| 2.4-$(Cl)_2$ | 8-$CO_2C_2H_5$ | H | 43 |
| 4-$OC_2H_5$ | 8-$CO_2C_2H_5$ | H | 45 |
| 4-$OCH_3$ | 8-$CO_2C_2H_5$ | H | 95 |
| 4-$OC_2H_5$ | 8-$CO_2C_3H_7$(iso) | H | 43 |
| H | 8-$CO_2C_2H_5$ | $C_2H_5CO-$ | 87 |
| 4-$OCH_3$ | 8-$CO_2C_2H_5$ | $CH_3CO-$ | 65 |
| 4-$OCH_3$ | 8-$CO_2C_2H_5$ | $C_2H_5CO-$ | 82 |
| 4-$OCH_3$ | 8-$CO_2C_2H_5$ | n-$C_3H_7CO-$ | 79 |
| 4-$OCH_3$ | 8-$CO_2C_2H_5$ | $CH_3$\\$CHCH_2CO-$ / $CH_3$ | 50 |
| 4-$OCH_3$ | 8-$CO_2C_2H_5$ | 2-$OCH_3$-Ph-CO- | 83 |
| H | 6-$CO_2C_2H_5$ | H | 53 |

TABLE 2-continued

[Structure: dibenzoxazepine with positions 1-9, O between 4a and 6a, CH₂ at position 11, N-R₃ at position 10; $(R_1)_n$ on left ring, $R_2'$ on right ring]

| $(R_1)_n$ Substituents | $R_2'$ | $R_3$ | Percent Inhibition of Platelet Aggregation % |
|---|---|---|---|
| 4-OCH₃ | 6-CO₂C₂H₅ | H | 48 | late (96 g) as colorless needles. (Yield: 77%, m.p. 121°–122° C.)

Elemental Analysis: Calcd. for $C_{17}H_{17}NO_4$: C, 68.21; H, 5.73; N, 4.68 (%); Found: C, 68.17; H, 5.84; N, 4.68 (%).

(b) By the procedure similar to that of (a) above, the compounds listed in the following Table 3 were prepared.

TABLE 3

[Structure: dibenzoxazepine with $(R_1)_n$ on left ring, $R_2'$ on right ring, N–H]

| | Substituents | | Yield | m.p. or b.p. | Elementary Analysis Calculated | | | Found | | |
|---|---|---|---|---|---|---|---|---|---|---|
| No. | $(R_1)_n$ | $R_2'$ | (%) | °C. | C | H | N | C | H | N |
| 1 | H | 8-CO₂C₂H₅ | 84 | 114–115 | $C_{16}H_{15}NO_3$ 71.36 | 5.61 | 5.20 | 71.41 | 5.60 | 5.28 |
| 2 | 2-Br | " | 72 | 143–144 | $C_{16}H_{14}BrNO_3$ 55.19 | 4.05 | 4.02 | 54.84 | 3.79 | 4.04 |
| 3 | 3-OCH₃ | " | 78 | 122–123 | $C_{17}H_{17}NO_4$ 68.21 | 5.73 | 4.68 | 68.18 | 5.60 | 4.82 |
| 4 | 2-OCH₃ | " | 77 | 113–114 | $C_{17}H_{17}NO_4$ 68.21 | 5.73 | 4.68 | 68.10 | 5.73 | 4.74 |
| 5 | 2-Cl | " | 76 | 162–163 | $C_{16}H_{14}ClNO_3$ 63.27 | 4.65 | 4.61 | 63.53 | 4.75 | 4.71 |
| 6 | 2,4-(Cl)₂ | " | 73 | 145–146 | $C_{16}H_{13}Cl_2NO_3$ 56.82 | 3.87 | 4.14 | 56.71 | 3.90 | 4.25 |
| 7 | 4-OC₂H₅ | " | 73 | 96–97 | $C_{18}H_{19}NO_4$ 61.33 | 6.11 | 4.47 | 61.41 | 6.23 | 4.56 |
| 8 | 2-CH₃ | " | 79 | 113–114 | $C_{17}H_{17}NO_3$ 72.06 | 6.05 | 4.94 | 71.98 | 5.95 | 4.77 |
| 9 | H | 6-CO₂C₂H₅ | 81 | 290–292 (0.01mmHg) | $C_{16}H_{15}NO_3$ 71.36 | 5.61 | 5.20 | 71.43 | 5.74 | 5.26 |

EXAMPLE 1

(a) A solution of ethyl 4-(2-formyl-6-methoxyphenoxy)-3-nitrobenzoate (145 g) in dioxane (1.2 l) and ethanol (150 ml) was hydrogenated over Raney nickel catalyst (60 ml) at room temperature under atmospheric pressure. After a pre-calculated amount of hydrogen was absorbed, the catalyst was removed by filtration and the filtrate was evaporated under reduced pressure. The residue was treated with ethanol (20 ml) to crystallize and then the separated crystals were collected by filtration. Recrystallization from ethanol gave ethyl 10,11-dihydro-4-methoxydibenz[b,f][1,4]oxazepine-8-caboxy-

EXAMPLE 2

(a) A mixture of ethyl 10,11-dihydrodibenz[b,f][1,4]oxazepine-8-carboxylate (5.4 g), potassium hydroxide (1.1 g), methanol (70 ml) and water (5 ml) was refluxed for 3 hours. After distilling off the solvents under reduced pressure, the residue was dissolved in distilled water (20 ml). The solution was washed with ethyl acetate and acidified with diluted hydrochloric acid. The separated crystals were collected by filtration and then recrystallized from methanol to give 10,11-dihydrodibenz[b,f][1,4]oxazepine-8-carboxylic acid. (Yield: 92%, m.p. 251°–252° C.)

Elemental Analysis: Calcd. for $C_{14}H_{11}NO_3$: C, 69.70; H, 4.60; N, 5.81 (%) Found: C, 69.58; H, 4.47; N, 5.79 (%).

(b) By the procedure similar to that of (a) above, the compounds listed in Table 4 were prepared.

TABLE 4

[Structure: dibenzoxazepine with $(R_1)_n$ on left ring, $R'_2$ on right ring, N–H]

| | Substituents | | Yield | m.p. | Elementary Analysis Calculated | | | Found | | |
|---|---|---|---|---|---|---|---|---|---|---|
| No. | $(R_1)_n$ | $R_2'$ | (%) | (°C.) | C | H | N | C | H | N |
| 1 | 2-Br | 8-CO₂H | 87 | 262–263 | $C_{14}H_{10}BrNO_3$ 52.52 | 3.15 | 4.38 | 52.48 | 3.22 | 4.31 |
| 2 | H | 6-CO₂H | 83 | 175–176 | $C_{14}H_{11}NO_3$ 69.70 | 4.60 | 5.81 | 69.65 | 4.67 | 5.77 |
| 3 | 3-OCH₃ | 8-CO₂H | 92 | 218–219 | $C_{15}H_{13}NO_4$ 66.41 | 4.83 | 5.16 | 66.38 | 4.77 | 4.99 |

TABLE 4-continued

[Structure: dibenz[b,f][1,4]oxazepine with $(R_1)_n$ and $R_2'$ substituents]

| No. | Substituents $(R_1)_n$ | $R_2'$ | Yield (%) | m.p. (°C.) | Elemental Analysis Calculated C H N | Found C H N |
|---|---|---|---|---|---|---|
| 4 | 4-OCH$_3$ | 8-CO$_2$H | 93 | 250–251 | C$_{15}$H$_{13}$NO$_4$ 66.41 4.83 5.16 | 66.68 4.62 5.25 |
| 5 | 2-OCH$_3$ | 8-CO$_2$H | 96 | 228–230 | C$_{15}$H$_{13}$NO$_4$ 66.41 4.83 5.16 | 66.57 4.75 5.32 |
| 6 | 2,4-(Cl)$_2$ | 8-CO$_2$H | 90 | 309–310 | C$_{14}$H$_9$Cl$_2$NO$_3$ 54.22 2.93 4.52 | 53.97 3.12 4.48 |
| 7 | 2-Cl | 8-CO$_2$H | 93 | 274–275 | C$_{14}$H$_{10}$ClNO$_3$ 60.99 3.66 5.08 | 61.10 3.78 5.14 |
| 8 | 4-OC$_2$H$_5$ | 8-CO$_2$H | 95 | 227–228 | C$_{16}$H$_{15}$NO$_4$ 67.36 5.30 4.91 | 67.53 5.41 4.85 |

EXAMPLE 3

To a mixture of thionyl chloride (10 g), benzene (10 ml) and three drops of pyridine was added 10,11-dihydrodibenz [b,f][1,4]oxazepine-6-carboxylic acid (1.2 g) while stirring. The mixture was heated to gradually elevate its temperature and then refluxed for 2 hours. The excess reagents were removed by distillation under reduced pressure and the residue was slowly added to isopropanol (20 ml) under ice cooling. After allowing the mixture to stand for one hour, isopropanol was distilled off under reduced pressure and the residue was recrystallized from ethanol to give isopropyl 10,11-dihydrobenz[b,f][1,4]oxazepine-6-carboxylate as colorless needles. (Yield: 78%) After converting to the corresponding hydrochloride and recrystallizing it from ethanol to give colorless needles. (m.p. 133°–144° C.)

Elemental Analysis: Calcd. for C$_{17}$H$_{17}$NO$_3$.HCl: C, 63.85; H, 5.67; N, 4.38 (%): Found: C, 63.58; H, 5.74; N, 4.35 (%).

EXAMPLE 4

(a) A mixture of 10,11-dihydro-4-methoxydibenz[b,f][1,4]oxazepine-8-carboxylic acid (3 g), isopropanol (30 ml) and concentrated sulfuric acid (0.5 ml) was refluxed for 10 hours and then the solvent used was distilled off. The residue was dissolved in ethyl acetate (50 ml) and, after washing with water, dried over anhydrous sodium sulfate. The solvent was distilled off and the residue was recrystallized from ethanol to give isopropyl 10,11-dihydro-4-methoxydibenz[b,f][1,4]oxazepine-8-carboxylate as colorless needles. (Yield: 90%, m.p. 109.5°–110.5° C.)

Elemental Analysis: Calcd. for C$_{18}$H$_{19}$NO$_4$: C, 68.99; H, 6.11; N. 4.47 (%): Found: C, 69.01; H, 6.18; N. 4.56 (%).

(b) By the procedure similar to that of (a) above, the compounds listed in Table 5 below were prepared.

TABLE 5

[Structure: dibenz[b,f][1,4]oxazepine with $(R_1)_n$ and $R_2'$ substituents]

| No. | Substituents $(R_1)_n$ | $R_2'$ | Yield (%) | m.p. (°C.) | Elemental Analysis Calculated C H N | Found C H N |
|---|---|---|---|---|---|---|
| 1 | H | 6-CO$_2$CH$_3$ | 85 | 102–103 | C$_{15}$H$_{13}$NO$_3$ 70.58 5.13 5.49 | 70.50 5.20 5.55 |
| 2 | 4-OCH$_3$ | 8-CO$_2$CH$_3$ | 95 | 104–105 | C$_{16}$H$_{15}$NO$_4$ 67.36 5.30 4.91 | 67.11 5.35 4.76 |
| 3 | 4-OCH$_3$ | 8-CO$_2$C$_3$H$_7$(n) | 95 | 89–90 | C$_{18}$H$_{19}$NO$_4$ 68.99 6.11 4.47 | 68.80 6.13 4.44 |
| 4 | 4-OCH$_3$ | 8-CO$_2$C$_4$H$_9$(n) | 97 | 104–105 | C$_{19}$H$_{21}$NO$_4$ 69.70 6.47 4.28 | 69.58 6.50 4.27 |
| 5 | 4-OC$_2$H$_5$ | 8-CO$_2$CH$_3$ | 90 | 115–116 | C$_{17}$H$_{17}$NO$_4$ 68.22 5.72 4.68 | 68.33 5.68 4.59 |
| 6 | 4-OC$_2$H$_5$ | 8-CO$_2$C$_3$H$_7$(iso) | 93 | 78–79 | C$_{19}$H$_{21}$NO$_4$ 69.71 6.47 4.28 | 69.57 6.53 4.34 |

EXAMPLE 5

(a) To a mixture of thionyl chloride (10 g), benzene (10 ml) and three drops of pyridine, was added 10,11-dihydrodibenz[b,f][1,4]oxazepine-8-carboxylic acid (1.2 g). The mixture was slowly heated to reflux temperature and refluxed for 2 hours. After distilling off the excess reagents, the residue was dissolved in chloroform (5 ml).

The solution was added dropwise to a mixture of m-aminobenzotrifluoride (0.8 g), chloroform (5 ml) and pyridine (5 ml) over 20 minutes while stirring under ice cooling and, after stirring at room temperature for 2 hours, it was washed with a diluted sodium hydroxide aqueous solution, diluted hydrochloric acid and water, and dried over anhydrous sodium sulfate. After distilling off the solvent under reduced pressure, the residue was recrystallized from ethanol to give 10,11-dihydrodibenz[b,f][1,4]oxazepine-8-carboxy[N-(3-trifluoromethylphenyl)] amide. (Yield: 78%, m.p. 171°-172° C.)

Elemental Analysis: Calcd. for $C_{21}H_{15}F_3N_2O_2$: C, 65.62; H, 3.93; N, 7.29 (%): Found: C, 65,58; H, 3.78; N, 7.31 (%).

(b) By the procedure similar to that of (a) above, the compounds listed in Table 6 below were prepared.

ml) over 15 minutes while stirring under ice cooling. The resulting mixture was stirred at room temperature for 3 hours, washed with a diluted sodium hydroxide aqueous solution and with water, dried over anhydrous sodium sulfate and distilled under reduced pressure to remove chloroform. The residue was recrystallized from ethanol to give ethyl N-benzoyl-10,11-dihydrodibenz[b,f][1,4]oxazepine-8-carboxylate as colorless needles.

TABLE 6

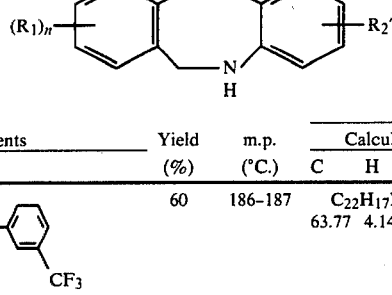

| No. | Substituents $(R_1)_n$ | $R_2'$ | Yield (%) | m.p. (°C.) | Elemental Analysis Calculated C H N | Found C H N |
|---|---|---|---|---|---|---|
| 1 | 4-OCH$_3$ | 8-CONH—⟨⟩—CF$_3$ | 60 | 186–187 | $C_{22}H_{17}F_3N_2O_3$ 63.77 4.14 6.76 | 63.50 4.23 6.58 |
| 2 | 3-OCH$_3$ | " | 67 | 191–192 | $C_{22}H_{17}F_3N_2O_3$ 63.77 4.14 6.76 | 63.66 4.31 6.65 |
| 3 | 2-OCH$_3$ | " | 72 | 177–178 | $C_{22}H_{17}F_3N_2O_3$ 63.77 4.14 6.76 | 63.71 4.27 6.64 |
| 4 | 4-OC$_2$H$_5$ | " | 78 | 173–174 | $C_{22}H_{19}F_3N_2O_3$ 64.48 4.47 6.54 | 64.54 4.56 6.48 |
| 5 | H | 8-CONH—⟨⟩ with CH$_3$, CH$_3$ | 68 | 177–178 | $C_{22}H_{20}N_2O_2$ 76.72 5.85 8.13 | 76.58 5.90 8.24 |
| 6 | H | 8-CONH—⟨⟩—OCH$_3$ | 73 | 189–190 | $C_{21}H_{18}N_2O_3$ 72.82 5.24 8.09 | 72.77 5.32 7.97 |

EXAMPLE 6

(a) To a solution of ethyl 10,11-dihydrodibenz[b,f][1,4]oxazepine-8-carboxylate (1.35 g) in a mixture of pyridine (2.5 ml) and chloroform (5 ml) was added dropwise a solution of benzoyl chloride (0.7 g) in chloroform (5 (Yield: 75%, m.p. 149°-150° C.)

Elemental Analysis: Calcd. for $C_{23}H_{19}NO_4$: C, 73.98; H, 5.13; N, 3.75 (%): Found: C, 73.68; H, 5.13; N, 3.77 (%).

(b) By the procedure similar to that of (a) above, the compounds listed in Table 7 below were prepared.

TABLE 7

| No. | Substituents $(R_1)_n$ | $R_2'$ | $R_3$ | Yield (%) | m.p. (°C.) | Elemental Analysis Calculated C H N | Found C H N |
|---|---|---|---|---|---|---|---|
| 1 | H | 8-CO$_2$C$_2$H$_5$ | ⟨⟩—CO— with CH$_3$ | 78 | 106–107 | $C_{24}H_{21}NO_4$ 74.40 5.46 3.62 | 74.34 5.55 3.61 |
| 2 | " | " | C$_2$H$_5$CO— | 95 | 95–96 | $C_{19}H_{19}NO_4$ 70.14 5.89 4.31 | 69.98 5.77 4.25 |
| 3 | " | " | ⟨⟩—CH$_2$CO— | 73 | 115–116 | $C_{24}H_{21}NO_4$ 74.40 5.46 3.62 | 74.36 5.42 3.58 |
| 4 | 4-OCH$_3$ | " | CH$_3$CO— | 92 | 78–79 | $C_{19}H_{19}NO_5$ 66.85 5.61 4.10 | 66.78 5.64 4.23 |
| 5 | " | " | C$_2$H$_5$CO— | 75 | 100–101 | $C_{20}H_{21}NO_5$ 67.59 5.96 3.94 | 67.42 6.00 4.09 |
| 6 | " | " | n-C$_3$H$_7$CO— | 86 | 121–122 | $C_{21}H_{23}NO_5$ 68.28 6.28 3.79 | 68.31 6.40 3.68 |
| 7 | " | " | iso-C$_3$H$_7$CO— | 72 | 148–149 | $C_{21}H_{23}NO_5$ 68.28 6.28 3.79 | 68.25 6.33 3.70 |
| 8 | " | " | (CH$_3$)$_2$CHCH$_2$CO— | 70 | 92–93 | $C_{22}H_{25}NO_5$ 68.91 6.57 3.65 | 68.85 6.61 3.58 |
| 9 | " | " | CH$_3$(CH$_2$)$_4$—CO— | 57 | 80–81 | $C_{23}H_{27}NO_5$ 69.50 6.80 3.52 | 69.44 6.78 3.61 |
| 10 | " | " | CH$_3$(CH$_2$)$_{12}$CO— | 98 | 62–63 | $C_{31}H_{43}NO_5$ 73.05 8.50 2.75 | 72.93 8.52 2.94 |

TABLE 7-continued

| No. | Substituents (R₁)ₙ | R₂' | R₃ | Yield (%) | m.p. (°C.) | Elemental Analysis Calculated C H N | Found C H N |
|---|---|---|---|---|---|---|---|
| 11 | " | " | CHCl₂CO— | 74 | 165–166 | $C_{19}H_{17}Cl_2NO_5$ 55.63 4.18 3.41 | 55.54 4.23 3.38 |
| 12 | " | " | CH₂Cl(CH₂)₂—CO— | 93 | 110–110.5 | $C_{21}H_{22}ClNO_5$ 62.45 5.49 3.47 | 62.71 5.54 3.50 |
| 13 | " | " | ⟨Ph⟩—CO— | 78 | 113–114.5 | $C_{24}H_{21}NO_5$ 71.45 5.25 3.47 | 71.52 5.30 3.38 |
| 14 | " | " | ⟨Ph⟩—CO— (3-CH₃) | 80 | 86–88 | $C_{25}H_{23}NO_5$ 71.93 5.55 3.36 | 72.04 5.63 3.42 |
| 15 | " | " | CH₃—⟨Ph⟩—CO— | 96 | 162–163 | $C_{25}H_{23}NO_5$ 71.93 5.55 3.36 | 71.79 5.62 3.32 |
| 16 | " | " | ⟨Ph⟩—CO— (OCH₃) | 91 | 159–160 | $C_{25}H_{23}NO_6$ 69.27 5.35 3.23 | 69.20 5.35 3.29 |
| 17 | " | " | CH₃O—⟨Ph⟩—CO— | 86 | 114.5–115.5 | $C_{25}H_{23}NO_6$ 69.27 5.35 3.23 | 69.21 5.40 3.34 |
| 18 | " | " | ⟨Ph⟩—CH₂CO— | 69 | 129–130 | $C_{25}H_{23}NO_5$ 71.93 5.55 3.36 | 71.85 5.51 3.32 |
| 19 | " | " | ⟨Ph⟩—CH=CHCO— | 94 | 115–116 | $C_{26}H_{23}NO_5$ 72.71 5.40 3.26 | 72.50 5.35 3.36 |
| 20 | " | " | ⟨Ph⟩—CO— (Cl) | 75 | 156–157 | $C_{24}H_{20}ClNO_5$ 65.28 4.60 3.20 | 66.01 4.63 3.24 |
| 21 | " | " | Cl—⟨Ph⟩—CO | 72 | 107–108 | $C_{24}H_{20}ClNO_5$ 65.83 4.60 3.20 | 65.56 4.68 3.22 |
| 22 | " | " | NO₂—⟨Ph⟩—CO— | 93 | 119–120 | $C_{24}H_{20}N_2O_7$ 64.28 4.50 6.25 | 64.30 4.61 -6.28 |
| 23 | 3-OCH₃ | " | CH₃CO— | 94 | 93–94 | $C_{19}H_{19}NO_5$ 66.85 5.61 4.10 | 66.94 5.70 4.09 |
| 24 | " | " | C₂H₅CO— | 87 | 128–129 | $C_{20}H_{21}NO_5$ 67.59 5.96 3.94 | 67.48 5.85 3.90 |
| 25 | " | " | ⟨Ph⟩—CO— | 91 | 125–126 | $C_{24}H_{21}NO_5$ 71.45 5.25 3.47 | 71.41 5.30 3.52 |
| 26 | " | " | ⟨Ph⟩—CO— (CH₃) | 92 | 135–136 | $C_{25}H_{23}NO_5$ 71.93 5.55 3.36 | 71.76 5.59 3.51 |
| 27 | 2-OCH₃ | " | C₂H₅CO— | 83 | 88–89 | $C_{20}H_{21}NO_5$ 57.59 5.96 3.94 | 67.38 6.02 3.88 |
| 28 | " | " | NO₂—⟨Ph⟩—CO— | 91 | 109–110 | $C_{24}H_{20}N_2O_7$ 64.28 4.50 6.25 | 64.33 4.62 6.30 |
| 29 | 2,4-(Cl)₂ | " | " | 53 | 146–147 | $C_{23}H_{16}Cl_2N_2O_6$ 56.69 3.31 5.75 | 56.73 3.44 5.69 |
| 30 | 2,4-(Cl)₂ | " | ⟨Ph⟩—CO— (CH₃) | 67 | 120–121 | $C_{24}H_{19}Cl_2NO_4$ 63.17 4.20 3.07 | 63.22 4.34 3.05 |
| 31 | 2-Cl | " | CH₃CO— | 84 | 120–121 | $C_{18}H_{16}ClNO_4$ 62.52 4.66 4.05 | 62.64 4.73 4.13 |
| 32 | " | " | C₂H₅CO— | 81 | 161–162 | $C_{19}H_{18}ClNO_4$ 63.43 5.04 3.89 | 53.56 5.14 3.83 |
| 33 | " | " | ⟨Ph⟩—CO— | 75 | 164–165 | $C_{23}H_{18}ClNO_4$ 67.73 4.45 3.43 | 67.69 4.51 3.46 |
| 34 | " | " | ⟨Ph⟩—CO— (CH₃) | 89 | 124–125 | $C_{24}H_{20}ClNO_4$ 68.33 4.78 3.32 | 68.40 4.83 3.44 |
| 35 | " | " | NO₂—⟨Ph⟩—CO— | 83 | 159–160 | $C_{23}H_{17}ClN_2O_6$ 61.00 3.78 6.19 | 60.88 3.80 6.21 |

TABLE 7-continued

| No. | (R₁)ₙ | R₂' | R₃ | Yield (%) | m.p. (°C.) | Calculated C H N | Found C H N |
|---|---|---|---|---|---|---|---|
| 36 | 4-OC$_2$H$_5$ | " | (3-methylbenzoyl) -CO- with CH$_3$ | 88 | 95-96 | C$_{26}$H$_{25}$NO$_5$ 72.37 5.84 3.25 | 72.40 5.93 3.32 |
| 37 | " | " | C$_2$H$_5$CO— | 85 | 93-94 | C$_{21}$H$_{23}$NO$_5$ 68.28 6.28 3.79 | 68.31 6.40 3.83 |
| 38 | " | " | (phenyl)-CO— | 79 | 95-96 | C$_{25}$H$_{23}$NO$_5$ 71.93 5.55 3.36 | 72.04 5.64 3.35 |
| 39 | " | " | NO$_2$-(phenyl)-CO— | 90 | 155-156 | C$_{25}$H$_{22}$N$_2$O$_7$ 64.93 4.80 6.06 | 65.04 4.92 5.98 |
| 40 | 4-OCH$_3$ | 8-CO$_2$H | (3-methylbenzoyl) -CO- with CH$_3$ | 78 | 117-118 | C$_{23}$H$_{19}$NO$_5$ 70.94 4.92 3.60 | 71.10 4.88 3.57 |

What is claimed is:

1. A dibenzoxazepine derivative represented by the formula (R$_1$)$_n$—[dibenz[b,f][1,4]oxazepine core with N-R$_3$]—COR$_2$ wherein R$_1$ is hydrogen, a halogen, a lower alkyl group or a lower alkoxyl group; n is an integer of 1 or 2; R$_2$ is a hydroxyl group, a lower alkoxyl group or a nuclear-substituted or unsubstituted anilino group; and R$_3$ is hydrogen or an carboxylic group.

2. Ethyl 10,11-dihydro-4-methoxydibenz[b,f][1,4]oxazepine-8-carboxylate according to claim 1.

3. Ethyl 10,11-dihydrodibenz[b,f][1;4]oxazepine-8-carboxylate according to claim 1.

4. Ethyl 10,11-dihydro-3-methoxydibenz[b,f][1,4]oxazepine-8-carboxylate according to claim 1.

5. Ethyl 10,11-dihydro-2-methoxydibenz[b,f][1,4]oxazepine-8-carboxylate according to claim 1.

6. Ethyl 10,11-dihydro-4-ethoxydibenz[b,f][1,4]oxazepine-8-carboxylate according to claim 1.

7. 10,11-Dihydrodibenz[b.f][1,4]oxazepine-6-carboxylic acid according to claim 1.

8. 10,11-Dihydro-4-methoxydibenz[b,f][1,4]oxazepine-8-carboxylic acid according to claim 1.

9. Isopropyl 10,11-dihydro-4-methoxydibenz[b,f][1,4]-oxazepine-6-carboxylate according to claim 1.

10. Methyl 10,11-dihydrodibenz[b,f][1,4-oxazepine-6-carboxylate according to claim 1.

11. Isopropyl 10,11-dihydro-4-ethoxydibenz[b,f][1,4]-oxazepine-8-carboxylate according to claim 1.

12. 10,11-Dihydro-4-methoxydibenz[b,f][1,4]oxazepine-8-carboxy(N-m-trifluoromethylphenyl)amide according to claim 1.

13. Ethyl 10,11-dihydro-N-(m-methylbenzoyl)-dibenz[b,f][1,4]-oxazepine-8-carboxylate according to claim 1.

14. Ethyl N-acetyl-10,11-dihydro-4-methoxydibenz[b,f][1,4]-oxazepine-8-carboxylate according to claim 1.

15. Ethyl 10,11-dihydro-4-methoxy-N-propionyldibenz[b,f][1,4]-oxazepine-8-carboxylate according to claim 1.

16. Ethyl N-n-butyryl-10,11-dihydro-4-methoxydibenz[b,f][1,4]-oxazepine-8-carboxylate according to claim 1.

17. Ethyl 10,11-dihydro-N-isobutyryl-4-methoxydibenz[b,f]-[1,4]oxazepine-8-carboxylate according to claim 1.

18. Ethyl 10,11-dihydro-N-isovaleryl-4-methoxydibenz[b,f]-[1,4]oxazepine-8-carboxylate according to claim 1.

19. Ethyl N-dichloroacetyl-10,11-dihydro-4-methoxydibenz[b,f][1,4]oxazepine-8-carboxylate according to claim 1.

20. Ethyl N-benzoyl-10,11-dihydro-4-methoxydibenz[b,f][1,4]-oxazepine-8-carboxylate according to claim 1.

21. Ethyl 10,11-dihydro-4-methoxy-N-(o-methoxybenzoyl)-dibenz[b,f][1,4]oxazepine-8-carboxylate according to claim 1.

22. Ethyl 10,11-dihydro-4-methoxy-N-(p-nitrobenzoyl)dibenz[b,f][1,4]oxazepine-8-carboxylate according to claim 1.

23. Ethyl 10,11-dihydro-3-methoxy-N-propionyldibenz[b,f]-[1,4]oxazepine-8-carboxylate according to claim 1.

24. Ethyl N-benzoyl-10,11-dihydro-3-methoxydibenz[b,f][1,4]-oxazepine-8-carboxylate according to claim 1.

* * * * *

UNITED STATES PATENT AND TRADEMARK OFFICE
CERTIFICATE OF CORRECTION

PATENT NO. : 4,290,953
DATED : September 22, 1981
INVENTOR(S) : KOIZUMI et al.

It is certified that error appears in the above-identified patent and that said Letters Patent are hereby corrected as shown below:

Column 3, Table 1, the structural formula should read:

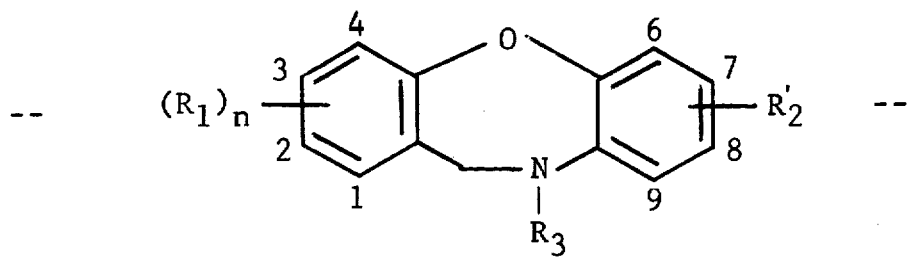

Signed and Sealed this

Seventh Day of September 1982

[SEAL]

Attest:

GERALD J. MOSSINGHOFF

Attesting Officer

Commissioner of Patents and Trademarks